United States Patent
Kawakita et al.

(10) Patent No.: US 6,591,692 B2
(45) Date of Patent: Jul. 15, 2003

(54) BEND-TEST DEVICE FOR WIRE HARNESSES

(75) Inventors: Yuki Kawakita, Yokkaichi (JP); Takuya Inoue, Yokkaichi (JP)

(73) Assignee: Sumitomo Wiring Systems, Ltd., Yokkaichi (JP)

( * ) Notice: Subject to any disclaimer, the term of this patent is extended or adjusted under 35 U.S.C. 154(b) by 0 days.

(21) Appl. No.: 09/814,708

(22) Filed: Mar. 23, 2001

(65) Prior Publication Data

US 2001/0024124 A1 Sep. 27, 2001

(30) Foreign Application Priority Data

Mar. 27, 2000 (JP) ........................................ 2000-085473

(51) Int. Cl.$^7$ ................................................ G01N 3/20
(52) U.S. Cl. ........................................... 73/851; 73/810
(58) Field of Search .......................... 73/781, 806, 808, 73/809, 810, 812, 849, 851, 856

(56) References Cited

U.S. PATENT DOCUMENTS

| | | | | |
|---|---|---|---|---|
| 1,951,908 A | * | 3/1934 | Hayford | 73/812 |
| 2,258,276 A | * | 10/1941 | Boettler | 73/812 |
| 3,518,877 A | * | 7/1970 | Collier | 73/809 |
| 3,629,783 A | * | 12/1971 | Holzwarth | 439/31 |
| 4,403,499 A | * | 9/1983 | Sack | 73/849 |
| 4,676,110 A | * | 6/1987 | Hodo | 73/809 |
| 4,979,396 A | * | 12/1990 | Carder | 73/812 |
| 5,879,047 A | | 3/1999 | Yamaguchi et al. | 296/146.7 |

FOREIGN PATENT DOCUMENTS

| | | | |
|---|---|---|---|
| FR | 2711241 | * | 4/1995 |
| JP | 52 72269 | * | 6/1977 |
| JP | 4-229506 | | 8/1992 |
| JP | 6-278460 | | 10/1994 |
| JP | 7-146226 | | 6/1995 |
| JP | 11263175 | | 9/1999 |

OTHER PUBLICATIONS

English Language Abstract of JP 7–146226.
English Language Abstract of JP 6–278460.
English Language Abstract of JP 11–263175.
English Language Abstract of JP 07–146226.
English Language Abstract of JP 6–278460.
English Language Abstract of JP 4–229506.

* cited by examiner

*Primary Examiner*—Christine Oda
(74) *Attorney, Agent, or Firm*—Greenblum & Bernstein P.L.C.

(57) ABSTRACT

A bend-test device for wire harnesses capable of handling a plurality of samples at the same time. The bend-test device includes a fixed frame unit, a hinge unit with a fulcrum axis, and a mobile frame unit connected to the fixed frame unit via the hinge unit in a freely pivotable manner around the fulcrum axis. The fixed frame unit includes fixed-side panels respectively including holder holes, each of which holds a grommet carrying a wire harness. The fixed-side panels are arranged in a parallel relation to each other, and aligned perpendicular to the direction of the fulcrum axis, in a freely mountable and removable manner. Likewise, the mobile frame unit includes mobile-side panels respectively including holder holes, each of which holds another grommet carrying the wire harness. The mobile-side panels are arranged as mentioned above, so that each of the mobile-side panels can be opposed to a corresponding one among the fixed-side panels. The bend-test device further includes a pivoting mechanism for reciprocatingly pivoting the mobile frame unit relative to the fixed frame unit around the fulcrum axis of the hinge unit.

4 Claims, 3 Drawing Sheets

BEND-TEST DEVICE FOR WIRE HARNESSES

BACKGROUND OF THE INVENTION

1. Field of the Invention

The present invention generally pertains to a device for estimating the lifetime of one or several wire harnesses subjected to repeated bending. The device allows a count of the number of repeated bending cycles prior to the breakage of the wire harnesses concerned. The count gives an estimation for the durability of the wire harnesses in question. Wire harnesses which are the subject-matter of the present invention are used e.g. in the doors of vehicles, where they are subjected to repeated bending.

2. Description of Background Information

Wire harnesses are employed, for example, for connecting diverse electrical apparatuses to a battery mounted in a vehicle. Such wire harnesses are formed by bundling together a plurality of electrical cables. When a door of a vehicle is opened or closed, or when an adjustable seat is slid back or forth, a wire harness employed therein is subjected to repeated bending forces. The latter are usually imparted on the wire harness through some localized bending sites therein. Studies on such a wire harness have already been described e.g. in Japanese Patent Applications published under Nos. Hei 4-229 506, Hei 6-278 460 and Hei 11-263 175.

In general, when a wire harness receives bending forces, there is a high risk that the localized bending sites mentioned above will be broken. The device of the present invention is contemplated to estimate the lifetime or durability of a wire harness including such localized bending sites.

As a common bend test, a relevant part of, e.g. a door of a vehicle is cut out as it is, and a wire harness is tested on that part. The number of bending cycles which leads to the breakage of the harness is then counted in order to estimate its durability.

In the above case however, the relevant part must be first procured from a car body, which requires time and expenses.

Accordingly, there is proposed a device simulating the above-mentioned relevant part of a car. Such a device includes two panels or frame units connected through a hinge unit. A wire harness is then held by a grommet, and the two panels or frame units are repeatedly opened and closed by means of a hydraulic cylinder. A device simulating a car's relevant part, as in the present case, is already disclosed e.g. in Japanese Patent Application published under No. Hei 7-146 226.

SUMMARY OF THE INVENTION

However, the above device can handle a bend test on only one sample at a time. Consequently, the same bend test has to be repeated many times, in order to collect a sufficient amount of test data. Such a method consumes much time and lacks efficiency.

It is therefore an object of the present invention to provide a bend test device for wire harnesses, capable of handling a plurality of samples at the same time.

To this end, there is provided a bend-test device for bending at least one wire harness repeatedly, in order to determine the number of bending cycles leading to a breakage in the wire harness. The bend-test device includes a first harness-holding unit, a second harness-holding unit and a hinge unit having a fulcrum axis, the first and second harness-holding units being connected through the hinge unit in a freely pivotable manner around the fulcrum axis.

According to the present invention, the first harness-holding unit includes a fixed frame unit including at least one first panel which carries at least one first holder configured to hold a wire harness. The first panel, when there are more than one, are arranged substantially in a parallel relation to each other, and aligned substantially perpendicularly to the direction of the fulcrum axis.

The second harness-holding unit includes a mobile frame unit including at least one corresponding second panel which carries at least one second holder configured to hold the wire harness. The at least one second panel is arranged in correspondence with the at least one first panel.

The bend-test device further includes a pivoting mechanism that pivots the mobile frame unit reciprocating manner relative to the fixed frame unit, so as to yield a predetermined pivoting angle around the fulcrum axis of the hinge unit.

Preferably, the hinge unit includes first and second hinge arms respectively including an elongate portion and an end portion.

The first and second hinge arms are preferably connected to each other around the fulcrum axis through the respective end portions, in a freely pivotable manner, and the first and second elongate portions respectively include several frame-fitting devices arranged in the length direction thereof, through which the fixed and mobile frame units can be linked to each other in a freely mountable and removable manner.

Preferably yet, each of the at least one first panel and the corresponding at least second panel includes several sizes of holders corresponding to different wire harness sizes to be tested.

Suitably, the fixed frame unit includes two elongated fixed members and two short fixed members, while the mobile frame unit includes two corresponding elongated and short mobile members.

The two elongated fixed members respectively include a first panel-fitting face with several panel-fitting device provided in a length direction thereof, while the two elongated mobile members respectively include a second panel-fitting face with several panel-fitting devices provided in a length direction thereof, whereby the first panel-fitting faces and the second panel-fitting faces are fitted with corresponding first panels and second panels.

One of the short fixed members and the corresponding short mobile member respectively include a hinge-fitting face with several arm-fitting means provided in a length direction thereof, through one of which is fixed the elongate portion of the corresponding hinge arm, such that the predetermined pivoting angle can be selected as desired.

BRIEF DESCRIPTION OF THE DRAWINGS

The above and the other objects, features and advantages of the present invention will be made apparent from the following description of the preferred embodiments, given as non-limiting examples, with reference to the accompanying drawings, in which.

DETAILED DESCRIPTION OF THE PREFERRED EMBODIMENTS

Figure 1:
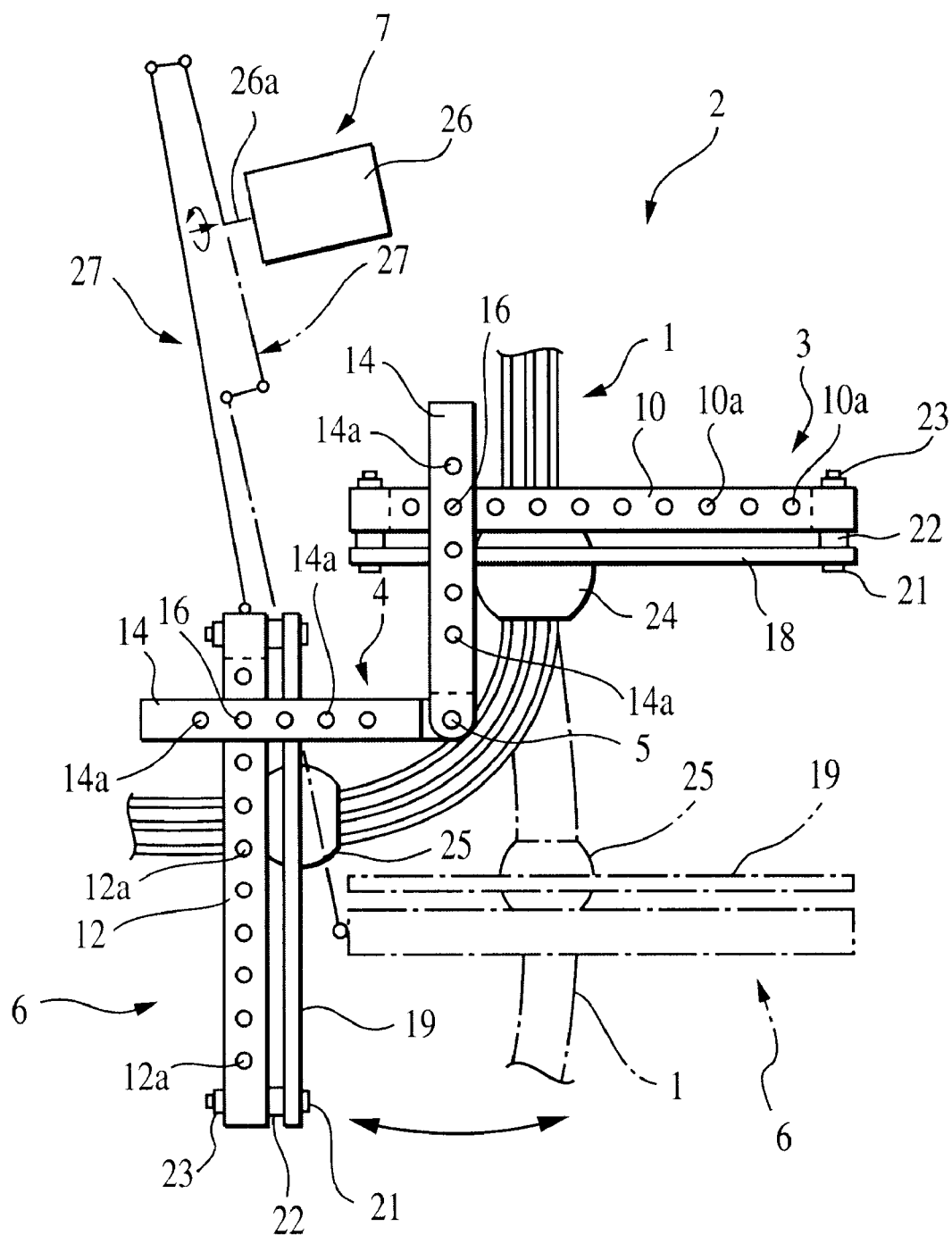
FIG. 1 is a top plan view of a bend-test device according to the present invention.

FIGS. 1 to 5 show an example of bend-test devices 2 used for testing wire harnesses 1 for installation in a vehicle door. The bend-test device includes a fixed frame unit 3 on which the functional parts of the device are mounted; a mobile frame unit 6 connected thereto through a hinge unit 4 and held around a fulcrum axis 5 in a freely pivotable manner; and a driver unit 7 for pivoting the mobile frame unit 6 around the fulcrum axis 5.

The fixed frame unit 3 includes first and second elongated fixed members 9 arranged in parallel relation to each other at a given separation, and first and second short fixed members 10 extending perpendicularly from corresponding end portions of the respective elongated fixed members. The fixed frame 3 thus forms a substantially rectangular shape standing vertically in normal use (see FIG. 2). The vertically lowest portion of the elongated fixed members 9 forms leg portions which can be installed on a floor in a freely engageable and removable manner.

The mobile frame unit 6 has a shape and a size substantially the same as those of the fixed frame unit 3, and includes elongated mobile members 11 and short mobile members 12. It stands with the elongated members vertical in normal use. In a typical embodiment, the fixed and mobile frame units 3 and 6 are about 1,000 mm long and about 30 mm wide.

When viewed in normal use (FIG. 2), one of the short fixed members 10 and one of the short mobile members 12 of the respective fixed and mobile frames 3 and 6 extend horizontally at the top of the latter. The short fixed and mobile members located atop both frame units include a number of arm-fitting holes 10a and 12a. They may be the female screw holes bored in the vertical direction (viewed in FIG. 2) at a given distance over the length of the short fixed and mobile members 10 and 12. Similarly, the elongated fixed and mobile members 9 and 11 of the respective fixed and mobile frame units 3 and 6 include a number of bolt-fitting holes 9a and 11a. They usually contain no internal screw and are bored in the horizontal direction (viewed in FIG. 2) at a given distance over the length of the long fixed and mobile members 9 and 11.

The hinge unit 4 includes a pair of hinge arms 14, in which an end portion of a first hinge arm 14 is connected to an end portion of a second hinge arm 14 through the fulcrum axis 5, and they are freely pivotable. The hinge arms 14 respectively include a number of bolt-fitting holes 14a, bored in the vertical direction (viewed in FIG. 2) at a given distance over the length of the hinge arms 14.

An appropriate bolt-fitting hole 14a in both hinge arms 14 is first selected. Corresponding bolts 16 are then fitted therethrough into correspondingly selected arm-fitting holes 10a and 12a in the respective fixed and mobile frames 3 and 6. The mobile frame unit 6 is thus supported by the fixed frame unit 3 around the fulcrum axis 5, which extends in the vertical direction (viewed in FIG. 2). Further, the mobile and fixed frame units 3 and 6 are combined in a freely pivotable manner.

The elongated fixed members 9 of the fixed frame unit 3 are mounted crosswise with one or several fixed-side panels (first panels) 18. The first panels 18 may have a rectangular shape. They are arranged at a given interval, perpendicular to the vertical direction of the fixed frame unit 3. Moreover, they are installed in a freely mountable and removable manner. Likewise, the elongated mobile members 11 of the mobile frame unit 6 are mounted crosswise with a plurality of mobile-side panels (second panels) 19. Likewise yet, the second panels 19 may have a rectangular shape, and are arranged at a given distance, perpendicular to the vertical direction of the mobile frame unit 6. They are also installed in a freely mountable and removable manner.

Figure 4:
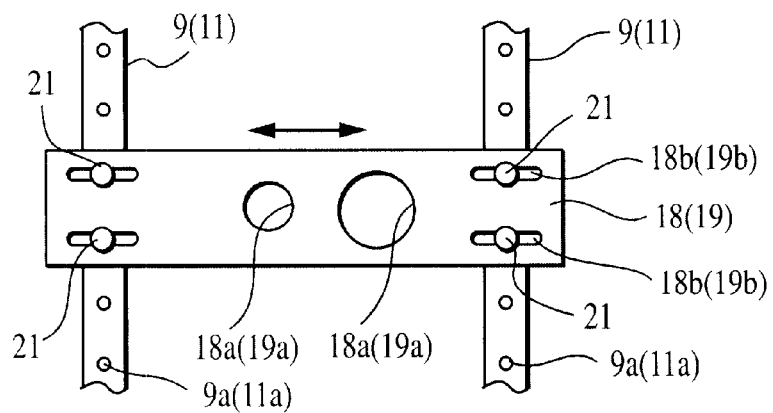
FIG. 4 is a front view illustrating how a fixed-side or mobile-side hold panel is mounted on a elongated member in the bend-test device of FIG. 2.
Figure 5:
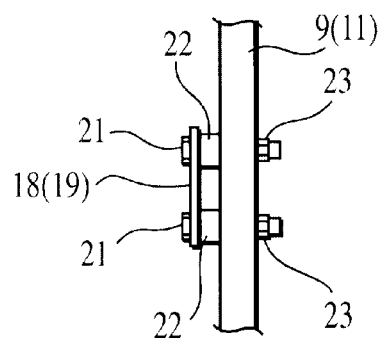
FIG. 5 is a side view of the fixed-side or mobile-side hold panel of FIG. 4.

As shown in FIGS. 4 and 5, the first and second panels 18 and 19 include grommet holes 18a and 19a serving as holders for different types of wire harnesses. These grommet holes 18a and 19a therefore have a diameter and thickness substantially the same as that of the holes fitted with the grommets used in a panel of a vehicle for the wire harness subject to the present bend tests. The first and second panels 18 and 19 further include bolt-fitting slots 18b and 19b (FIG. 4) respectively, bored horizontally at four corners of the first and second panels 18 and 19. The bolt-fitting slots 18b and 19b are then fitted with bolts 21.

The bolts 21, fitted into the bolt-fitting slots 18b and 19b, are inserted through a position-adjustable spacer 22 having an appropriate spacing length. They are farther inserted into the bolt-fitting holes 9a and 11a suitably selected among those arranged over the length of the elongated fixed and mobile members 9 and 11. The bolts 21 are then fixed with nuts 23.

Spacers 22 having different spacing lengths are prepared beforehand. Among them, a spacer 22 is selected such that the mounting configuration between a first panel 18 and a second panel 19 corresponds to that of the simulated vehicle.

The grommet holes 18a and 19a in the first and second panels 18 and 19 are mounted with grommets 24 and 25 corresponding to those used in a simulated vehicle. A wire harness 1 is thus held between the two grommets 24 and 25.

The drive unit 7 includes a driving motor 26 including a servomotor capable of altering and controlling the rotation speed. The drive unit 7 further includes a crank mechanism 27 which links the rotary spindle 26a of the driving motor 26 to the elongated mobile members 11 of the mobile frame unit 6, and is put into motion in synchronization therewith. In this construction, the rotary spindle 26a is first rotated by the driving motor 26. The mobile frame unit 6 is then pivoted around the fulcrum axis 5 through the crank mechanism 27 (see broken lines in FIG. 1) at a predetermined pivoting angle. The pivoting movement can thus be reciprocated very easily.

The cranks used in the crank mechanism 27 are provided in different lengths. Accordingly, when the mobile frame unit 6 is subjected to reciprocating movement relative to the fixed frame unit 3, the pivoting angles between the two frames (i.e. angles when they are opened and closed) can be adjusted at will by choosing the length of a crank.

When a wire harness 1 is subjected to such a bend-test device 2, the first and second panels 18 and 19 including the grommets holes 18a and 19a are chosen so as to correspond respectively to that of a body-panel and that of a vehicle door. The first and second panels 18 and 19 are then fitted to the elongated fixed and mobile members 9 and 11, respectively, by using bolts 21, spacers 22 and nuts 23. When fixing, the bolt-fitting holes 9a and 11a and spacers 22 are selected such that the configuration of the grommet holes 18a in the first panel 18, relative to the grommet holes 19a in the second panel 19, correspond to that of the simulated automobile. The horizontal positions can be adjusted by the bolt-fitting slits 18b and 19b (FIG. 4).

Figure 2:
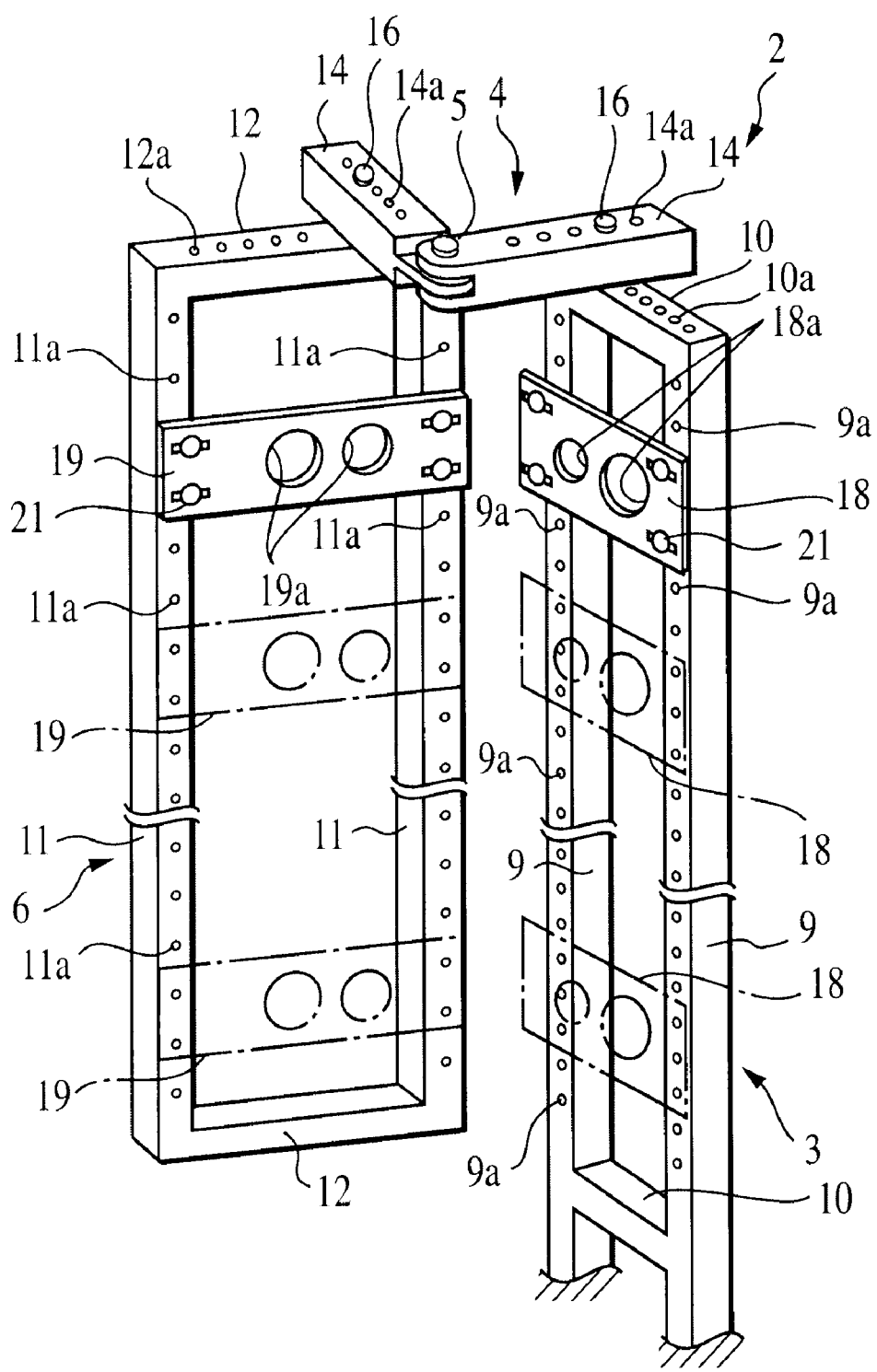
FIG. 2 is a perspective elevational view of the bend-test device of the invention.
Figure 3:
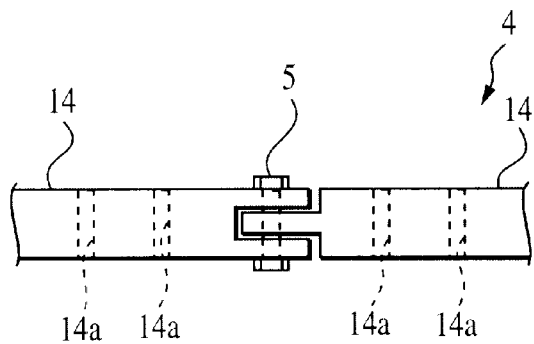
FIG. 3 is a side view of the hinge portion of the bend-test device of FIG. 2.

As shown in broken lines in FIG. 2, more than one first and second panels 18 and 19 are usually mounted in the vertical direction of the fixed and mobile frame units 3 and 6, such that each configuration corresponds to an actual arrangement of a simulated vehicle.

Thus, the grommets 24 and 25 are fitted into the corresponding grommet holes 18a and 19a, while a wire harness 1 is held through the grommets 24 and 25. This construction simulates the configuration in which a wire harness 1 is wired between an opening and closing door and a nearby body panel in a simulated vehicle. In this manner, a plurality of such constructions are obtained in the vertical direction.

When the driving motor 26 is put into motion thereafter, the mobile frame unit 6 (which simulates a door) is subjected to reciprocating movements via the crank mechanism 27. Several bend tests for wire harnesses can thus be performed at the same time.

The breakage of each electrical cable contained in each wire harness 1 is then detected. Accordingly, one bend test yields data for a plurality of samples. The bend-test time for collecting sufficient data can thus be shortened greatly, and the working efficiency is also improved correspondingly.

The breakage of each electrical cable can be detected by a known method, e.g. method described in Japanese Patent Application published under No. Hei 7-146 226.

As described above, when it is known how a wire harness 1 is wired in a vehicle, the mounting positions of the hinge unit 4, fixed-side panel (first panel) 18 and mobile-side panel (second panel) 19, as well as the angles when the mobile frame unit 6 is opened and closed, can be adjusted accordingly. In this fashion, the actual bending and stretching behavior in a vehicle can be simulated in a very precise manner. Further, the inventive device can be adapted to various types of vehicles having different mounting configurations, by modifying the mounting configuration of the device. The inventive device thus has a wide range of applications.

Furthermore, the bend-test device of the invention may be used in a thermostatic or high temperature enclosure. The applicable range of the device can thus be further widened.

Each wire harness 1 and the driving power source circuit for the driving motor 26 may be connected electrically, so that when one of the wire harnesses is cut, the driving motor 26 is halted. In this manner, the number of bending cycles performed up to the harness breakage point can be detected easily.

In the above embodiments, the driving motor 26 is exemplified as a pivoting drive unit 7. However, an actuator such as hydraulic cylinder may also be used.

The mobile frame of the invention can simulate not only a door of a vehicle, but also a slide seat of a vehicle or some other mobile parts in a vehicle. Further, the door, slide seat or mobile parts are not limited to those installed in an automobile.

Further, in the above embodiments, a wire harness 1 is illustrated as including a plurality of electrical cables. However, the wire harness 1 may also include one or several flexible flat cables.

Furthermore, the arm-fitting holes 10a and 12a formed in the short fixed and mobile members 10 and 12 are illustrated as female screw holes (the inside wall of the hole is screwed). The latter may thus be fitted with a corresponding bolt including e.g. a male screwed end. However, the arm-fitting holes may also be bolt-fitting holes (without inside screw), and the bolts used may be fixed by screwing nuts. Conversely, as shown in FIG. 2 (see also 14a in FIG. 3), bolt-fitting holes 9a and 11a are formed in the long fixed and mobile members 9 and 11. Instead, they may be replaced by female screw holes, which are then fitted with bolts having a male screwed end.

As mentioned above, the invention relates to a bend-test device for bending wire harnesses repeatedly and obtaining the number of bending cycles leading to the breakage of the wire harnesses. The bend-test device may include a fixed frame unit, a hinge unit with a fulcrum axis, and a mobile frame unit connected to the fixed frame unit via the hinge unit in a freely pivotable manner around the fulcrum axis. The fixed frame unit may include a plurality of fixed-side panels respectively including holders respectively configured to hold one of the wire harnesses. The plurality of fixed-side panels may be arranged in a parallel relation to each other, and aligned perpendicularly to the fulcrum axis over the length thereof, in a freely mountable and removable manner. The mobile frame unit may include a plurality of mobile-side panels respectively including holder means respectively adapted for holding one of the wire harnesses. The plurality of mobile-side panels may be arranged in a parallel relation to each other, and aligned perpendicularly to the fulcrum axis over the length thereof, in a freely mountable and removable manner, so that each of the plurality of mobile-side panels can be opposed to a corresponding one among the plurality of fixed-side panel. Further, the device may include a pivoting mechanism for reciprocatingly pivoting the mobile frame unit relative to the fixed frame unit around the fulcrum axis of the hinge unit.

A single bend test thus gives data for a plurality of samples. The time for data collection is thus shortened, and the test efficiency is greatly improved.

Further, the hinge unit may include a pair of hinge arms having a respective elongate portion and end portion. The pair of hinge arms may be connected to each other through the respective end portions, joined around the fulcrum axis in a freely pivotable manner. The respective elongate portions of the hinge arms may include several fitting points therealong, through which the fixed frame unit and mobile frame units can be linked to each other in a freely mountable and removable manner. Each of the fixed-side panels and mobile-side panels may include several types of harness holders.

By modifying or adjusting the mounting configuration, the inventive device can be adapted to various mounting configurations and bending conditions, thereby enjoying a wide variety of use conditions.

Although the invention has been described with reference to particular means, materials and embodiments, it is to be understood that the invention is not limited to the particulars disclosed and extends to all equivalents within the scope of the claims.

The present disclosure relates to subject matter contained in priority Japanese Application No. 2000-085473, filed on Mar. 27, 2000.

What is claimed:

1. A bend-test device for bending at least one wire harness repeatedly, in order to determine the number of bending cycles leading to a breakage in the wire harness, said bend-test device comprising:

a first harness-holding unit, a second harness-holding unit and a hinge unit having a fulcrum axis, said first and second harness-holding units being connected through said hinge unit in a freely pivotable manner around said fulcrum axis;

said first harness-holding unit comprising a fixed frame unit including at least one first panel carrying at least one first holder configured to hold a wire harness, said at least one first panel aligned substantially perpendicularly to the direction of said fulcrum axis;

said second harness-holding unit comprising a mobile frame unit including at least one second panel carrying at least one second holder configured to hold said wire harness, said at least one second panel being arranged to correspond to said at least one first panel; and said bend-test device further comprising a pivoting mechanism for pivoting said mobile frame unit reciprocatingly, relative to said fixed frame unit, such as to yield a predetermined pivoting angle around said fulcrum axis of said hinge unit;

wherein said fixed frame unit comprises two elongated fixed members and two short fixed members, while said mobile frame unit comprises corresponding two elongated and short mobile members;

said two elongated fixed members respectively comprise a first panel-fitting face with several panel-fitting devices provided in a length direction thereof, while said two elongated mobile members respectively comprise a second panel-fitting face with several panel-fitting devices provided in a length direction thereof, whereby said first panel-fitting faces and said second panel-fitting faces are fitted with corresponding first panels and second panels; and one of said short fixed members and the corresponding short mobile member respectively comprise a hinge-fitting face with several arm-fitting devices provided in a length direction thereof, through one of which is fixed said elongate portion of the corresponding hinge arm, such that said predetermined pivoting angle can be selected as desired.

2. A bend-test device for bending at least one wire harness repeatedly, in order to determine the number of bending cycles leading to a breakage in the wire harness, said bend-test device comprising:

a first harness-holding unit, a second harness-holding unit and a hinge unit having a fulcrum axis, said first and second harness-holding units being connected through said hinge unit in a freely pivotable manner around said fulcrum axis;

said first harness-holding unit comprising a fixed frame unit including at least one first panel carrying at least one first holder configured to hold a wire harness, said at least one first panel aligned substantially perpendicularly to the direction of said fulcrum axis;

said second harness-holding unit comprising a mobile frame unit including at least one second panel carrying at least one second holder configured to hold said wire harness, said at least one second panel being arranged to correspond to said at least one first panel;

said hinge unit comprising first and second hinge arms respectively including an elongate portion and an end portion, said first and second hinge arms being connected to each other around said fulcrum axis through said respective end portions, in a freely pivotable manner, said first and second elongate portions respectively comprising several frame-fitting devices arranged in the length direction thereof, through which said fixed and mobile frame units can be linked to each other in a freely mountable and removable manner; and said bend-test device further comprising a pivoting mechanism for pivoting said mobile frame unit reciprocatingly, relative to said fixed frame unit, such as to yield a predetermined pivoting angle around said fulcrum axis of said hinge unit;

wherein said fixed frame unit comprises two elongated fixed members and two short fixed members, while said mobile frame unit comprises corresponding two elongated and short mobile members;

said two elongated fixed members respectively comprise a first panel-fitting face with several panel-fitting devices provided in a length direction thereof, while said two elongated mobile members respectively comprise a second panel-fitting face with several panel-fitting devices provided in a length direction thereof, whereby said first panel-fitting faces and said second panel-fitting faces are fitted with corresponding first panels and second panels; and one of said short fixed members and the corresponding short mobile member respectively comprise a hinge-fitting face with several arm-fitting devices provided in a length direction thereof, through one of which is fixed said elongate portion of the corresponding hinge arm, such that said predetermined pivoting angle can be selected as desired.

3. A bend-test device for bending at least one wire harness repeatedly, in order to determine the number of bending cycles leading to a breakage in the wire harness, said bend-test device comprising:

a first harness-holding unit, a second harness-holding unit and a hinge unit having a fulcrum axis, said first and second harness-holding units being connected through said hinge unit in a freely pivotable manner around said fulcrum axis;

said first harness-holding unit comprising a fixed frame unit including at least one first panel carrying at least one first holder configured to hold a wire harness, said at least one first panel aligned substantially perpendicularly to the direction of said fulcrum axis;

said second harness-holding unit comprising a mobile frame unit including at least one second panel carrying at least one second holder configured to hold said wire harness, said at least one second panel being arranged to correspond to said at least one first panel, wherein each of said at least one first panel and the corresponding at least second panel comprises several sizes of holders corresponding to different wire harness sizes to be tested; and said bend-test device further comprising a pivoting mechanism for pivoting said mobile frame unit reciprocatingly, relative to said fixed frame unit, such as to yield a predetermined pivoting angle around said fulcrum axis of said hinge unit;

wherein said fixed frame unit comprises two elongated fixed members and two short fixed members, while said mobile frame unit comprises corresponding two elongated and short mobile members;

said two elongated fixed members respectively comprise a first panel-fitting face with several panel-fitting devices provided in a length direction thereof, while said two elongated mobile members respectively comprise a second panel-fitting face with several panel-fitting devices provided in a length direction thereof, whereby said first panel-fitting faces and said second panel-fitting faces are fitted with corresponding first panels and second panels; and one of said short fixed members and the corresponding short mobile member respectively comprise a hinge-fitting face with several arm-fitting devices provided in a length direction thereof, through one of which is fixed said elongate portion of the corresponding hinge arm, such that said predetermined pivoting angle can be selected as desired.

4. A bend-test device for bending at least one wire harness repeatedly, in order to determine the number of bending cycles leading to a breakage in the wire harness, said bend-test device comprising:

a first harness-holding unit, a second harness-holding unit and a hinge unit having a fulcrum axis, said first and second harness-holding units being connected through said hinge unit in a freely pivotable manner around said fulcrum axis;

said first harness-holding unit comprising a fixed frame unit including at least one first panel carrying at least one first holder configured to hold a wire harness, said at least one first panel aligned substantially perpendicularly to the direction of said fulcrum axis;

said second harness-holding unit comprising a mobile frame unit including at least one second panel carrying at least one second holder configured to hold said wire harness, said at least one second panel being arranged to correspond to said at least one first panel, wherein each of said at least one first panel and the corresponding at least second panel comprises several sizes of holders corresponding to different wire harness sizes to be tested;

said hinge unit comprising first and second hinge arms respectively including an elongate portion and an end portion, said first and second hinge arms being connected to each other around said fulcrum axis through said respective end portions, in a freely pivotable manner, said first and second elongate portions respectively comprising several frame-fitting devices arranged in the length direction thereof, through which said fixed and mobile frame units can be linked to each other in a freely mountable and removable manner; and said bend-test device further comprising a pivoting mechanism for pivoting said mobile frame unit reciprocatingly, relative to said fixed frame unit, such as to yield a predetermined pivoting angle around said fulcrum axis of said hinge unit;

wherein said fixed frame unit comprises two elongated fixed members and two short fixed members, while said mobile frame unit comprises corresponding two elongated and short mobile members;

said two elongated fixed members respectively comprise a first panel-fitting face with several panel-fitting devices provided in a length direction thereof, while said two elongated mobile members respectively comprise a second panel-fitting face with several panel-fitting devices provided in a length direction thereof, whereby said first panel-fitting faces and said second panel-fitting faces are fitted with corresponding first panels and second panels; and one of said short fixed members and the corresponding short mobile member respectively comprise a hinge-fitting face with several arm-fitting devices provided in a length direction thereof, through one of which is fixed said elongate portion of the corresponding hinge arm, such that said predetermined pivoting angle can be selected as desired.

* * * * *